(12) United States Patent
Rodriguez-Kabana et al.

(10) Patent No.: US 8,197,834 B2
(45) Date of Patent: Jun. 12, 2012

(54) SOLID FORMULATIONS OF HYDROGEN CYANAMIDE FOR AGRICULTURAL APPLICATIONS

(75) Inventors: Rodrigo Rodriguez-Kabana, Auburn, AL (US); Anne E. V. Gorden, Auburn, AL (US)

(73) Assignee: Metbro Distributing L.P., Fresno, CA (US)

( * ) Notice: Subject to any disclaimer, the term of this patent is extended or adjusted under 35 U.S.C. 154(b) by 902 days.

(21) Appl. No.: 11/864,148

(22) Filed: Sep. 28, 2007

(65) Prior Publication Data

US 2009/0087467 A1   Apr. 2, 2009

(51) Int. Cl.
*A01N 25/12*   (2006.01)
(52) U.S. Cl. ..................................................... 424/409
(58) Field of Classification Search ............... None
See application file for complete search history.

(56) References Cited

U.S. PATENT DOCUMENTS

| | | | |
|---|---|---|---|
| 4,059,700 A * | 11/1977 | Lindsay | ............ 514/127 |
| 4,259,344 A | 3/1981 | Gonczi et al. | |
| 5,013,762 A | 5/1991 | Smith et al. | |
| 5,045,105 A | 9/1991 | Grossmann et al. | |
| 5,084,477 A | 1/1992 | Walter et al. | |
| 5,693,591 A | 12/1997 | North et al. | |
| 5,726,129 A | 3/1998 | Barnes et al. | |
| 5,885,932 A | 3/1999 | Parr et al. | |
| 6,358,312 B1 | 3/2002 | Tanner et al. | |
| 6,746,988 B2 | 6/2004 | Hopkinson et al. | |
| 6,852,341 B2 | 2/2005 | Rodriguez-Kabana | |
| 6,878,389 B2 | 4/2005 | Rodriguez-Kabana | |
| 6,932,985 B2 | 8/2005 | Rodriguez-Kabana | |
| 2007/0116781 A1 | 5/2007 | Rodriguez-Kabana | |
| 2007/0149409 A1 | 6/2007 | Burnet et al. | |

OTHER PUBLICATIONS

Daniel, P. et. al.; "Uber die Anwendung chemischer Mittel zum Vorwelken von Futterpflanzen" 1973, Wirtschaftseiqene Futter, vol. 19, No. 4, pp. 269-281, including English translation.*

* cited by examiner

*Primary Examiner* — David J Blanchard
*Assistant Examiner* — Kortney L Klinkel
(74) *Attorney, Agent, or Firm* — Kilpatrick Townsend & Stockton LLP.; M. Henry Heines (57) ABSTRACT

Agricultural crops are protected from the growth of weeds and other undesirable organisms by the application of hydrogen cyanamide in a granular formulation.

25 Claims, 4 Drawing Sheets

SOLID FORMULATIONS OF HYDROGEN CYANAMIDE FOR AGRICULTURAL APPLICATIONS

BACKGROUND OF THE INVENTION

1. Field of the Invention

This invention resides in materials and methods for crop protection, and is particularly concerned with soil treatments to control the growth of organisms, such as insects, fungi, and weeds, that are deleterious to crop growth.

2. Description of the Prior Art

The agricultural industry relies on effective control of insects, plant pathogens, nematodes, and weeds, for bountiful and healthy crops. One means of achieving this control is by treatment of the crops with cyanamide for both stimulation of crop growth and protection of crops from insect pests, plant pests, and fungi. Cyanamide, a term that is used to designate both hydrogen cyanamide ($H_2N-C\equiv N$) and calcium cyanamide ($Ca^{++}\text{=}N-C\equiv N$), is used particularly in Europe as an herbicide and in various parts of the world as a plant growth regulator. From its introduction in the 1950's, cyanamide has been used as a pre-emergence herbicide and a defoliant. Research has shown that the active ingredient of both hydrogen cyanamide and calcium cyanamide preparations is hydrogen cyanamide itself, with the effectiveness of calcium cyanamide being attributable at least in part to the action of moist soil on plants in hydrolyzing calcium cyanamide to hydrogen cyanamide. Hydrogen cyanamide has traditionally been applied as an aqueous liquid formulation due to the ease in which aqueous hydrogen cyanamide decomposes to urea and is then converted to ammoniacal forms of nitrogen and carbon dioxide. These metabolites serve as plant nutrients and their formation is mediated by biological organisms, physical processes, or both.

Liquid agricultural formulations suffer from certain limitations, however. In liquid cyanamide formulations, the cyanamide slowly decomposes to urea and other decomposition products, even when the formulations are kept in sealed containers. The rate of decomposition can be lessened to some degree by buffering the formulation with carboxylic acids or phosphoric acid, but not stopped entirely. Despite this, phosphoric acid has been used to some success, but in drip irrigation systems, hydrogen cyanamide formulations that contain phosphoric acid and water with a high calcium content cause plugging of the drip emitters. Plugging is also observed in spray systems that utilize spray nozzles with small diameters. Plugging can also be caused by other active ingredients and additives, upon exposure of the liquid formulation to conditions such as temperature changes and high shear stress. New additives have been developed to address this problem and to otherwise improve the formulation such as by enhancing the spreading of the active ingredient(s), but the inclusion of auxiliary chemicals in agrochemical compositions is closely regulated by the Environmental Protection Agency, and it is increasingly difficult to obtain approval of formulated compositions. In addition, the application of a liquid formulation typically requires an irrigation system, which is not available in all crop areas. Still further, while it is often desirable to combine two or more active ingredients in a single formulation for simultaneous application, certain actives are not compatible with aqueous solutions.

SUMMARY OF THE INVENTION

It has now been discovered that hydrogen cyanamide can be applied as a solid formulation with the same or approximately the same efficacy against undesirable organisms. The solid formulation is a porous granule impregnated with hydrogen cyanamide. The granule can be prepared by allowing the pores of the granule to absorb a liquid solution of hydrogen cyanamide, then drying the granule to remove all or substantially all of the solvent, and applying the dry granule directly to the soil or crop. An advantage of the solid formulation is that application of the formulation does not require an irrigation system, and can be done on narrowly focused areas if desired. A further advantage is that the formulation is significantly less susceptible to moisture-induced decomposition since the granule tends to isolate the molecules of hydrogen cyanamide molecules from those of water. The rate of decomposition can be lowered even further by storing the cyanamide-impregnated granules in sealed containers. Still further, the granule form provides a means for controlled or sustained release of the active material, prolonging the efficacy of the material and lessening the harm to crop plants by avoiding spikes in concentration. This lowered rate of release extends the utility of the impregnated granule to post-emergence applications and to applications where low concentrations are desired, such as turf maintenance. A still further advantage is that the impregnated granule is more physically stable and less prone to dust formation during handling than powdered hydrogen cyanamide or dry formulations in general that do not utilize a porous granule as a support matrix. The granule can also be combined with any other active ingredients, whether wet or dry, water-soluble or not. Novelty resides in the solid formulation as a composition of matter, in methods of preparing the formulation by impregnating porous granules with hydrogen cyanamide, and in the application of the formulation to soil, both pre-emergence and post-emergence, as methods of use.

Still further discoveries, objects, and advantages of the invention will be apparent from the description that follows.

DETAILED DESCRIPTION OF THE INVENTION AND PREFERRED EMBODIMENTS

The term "hydrogen cyanamide" is used herein to denote a compound of the formula This compound is also referred to among chemists as cyanamide, cyanogenamide, and carbodiimide, and is to be distinguished from the calcium salt, calcium cyanamide Hydrogen cyanamide is commercially available and can be obtained from a supplier of industrial chemicals, or it can be prepared by conventional synthesis methods, notably the continuous carbonation of calcium cyanamide. When hydrogen cyanamide is supplied in aqueous solution, a stabilizer can be included in the solution since the hydrogen cyanamide is susceptible to decomposition through hydrolysis. As noted above, a phosphate buffer in the form of phosphate ion or phosphoric acid is often used as the stabilizer. Alternatively, however, and preferably in many cases, the phosphate buffer can be either substantially or entirely eliminated, and in further cases, no stabilizer at all is included. Thus, in certain embodiments of the invention, the formulation is applied to the soil or the agricultural site with at most a trace amount of phosphate ion or other stabilizer, or in certain further embodiments, devoid of phosphate ion, or of any stabilizers. The term "trace amount" is used herein to mean 1,000 ppm or less, preferably 100 ppm or less.

In certain embodiments of the invention, the hydrogen cyanamide is combined with other agriculturally active ingredients, such as other pesticides (herbicides, insecticides, or fungicides, or combinations thereof), plant growth regulators, defoliants, or fertilizers. Adjuvants or diluents are also included in certain embodiments. Examples of such adjuvants are formulating aids, buffers and other stabilizers, solubilizing agents, and dispersing agents. These materials are well known in the agricultural formulations industry and readily available from suppliers of agricultural chemicals. Any of these additional substances can be included in the pores of the granules in admixture with the hydrogen cyanamide, or in separate granules, or in solid or liquid phases that are applied either simultaneously with the hydrogen cyanamide or as a supplemental application within a short period of time of the application of the hydrogen cyanamide granules. In certain embodiments, the hydrogen cyanamide is the sole biologically active ingredient. By "sole biologically active ingredient" is meant that no other ingredients are present that either promote or inhibit the growth of organisms, including crop plants as well as undesirable organisms, or that kill all or a portion of otherwise viable organisms.

The solid granules can be formed of any porous solid that is compatible with, yet chemically inert to, the hydrogen cyanamide and wettable by the solvent used during impregnation with hydrogen cyanamide. Examples of such solids are crushed sandstone, crushed limestone, calcined diatomaceous earth, crushed brick, crushed shale, and calcined clay. Calcined clay is a preferred material. Examples of clays that can be calcined for use in this invention are those containing significant quantities of montmorillonite or illite, and silica. Other smectite clays such as bentonite, beidellite, nontronite, hectorite, saponite, attapulgite, and sepiolite, can also be used. Phyllosilicates, such as antigorite, chrysolite, kaolinite, talc, pyrophyllite, muscovite, biolite, lepidolite, margarite, and chlorite, can also be used. When silica is present, it may be in either crystalline or amorphous form. Crystalline forms include quartz, cristobalite, tridymite, coesite, stishovite, melanophlogite, moganite, and silhydrite, while non-crystalline forms include opal-CT, opal-C, and opal $A_N$. Examples of calcined clay granules that are particularly useful are those sold under the name PROFILE™, available from Profile Products L.L.C., Buffalo, N.Y., USA, and described in U.S. Pat. No. 6,096,126 (Tanner et al., issued Aug. 1, 2000) and U.S. Pat. No. 6,155,749 (Tanner et al., issued Dec. 5, 2000).

The porosity of the granules can vary and is not critical to the invention other than that sufficient porosity be present to retain the amount of the hydrogen cyanamide needed for a particular agricultural application. The porosity can be expressed as the pore space, or percent pore volume, and in preferred embodiments, the pore space is from about 30% to about 90%, more preferably from about 50% to about 90%, and most preferably from about 60% to about 85%. The percent capillary porosity, which is defined as the percent pore space that is in the form of capillary pores, i.e., pores that are open to the surface of the granule, is preferably at least about 20%, more preferably at least about 40%, and most preferably from about 40% to about 80%. The porosity of the particles is closely associated with cation exchange capacity (CEC). In preferred embodiments, the CEC is from about 10 meq/100 g to about 75 meq/100 g. The granule size can vary as well. In preferred embodiments, at least about 75% of the granules have particle diameters of from about 0.1 mm to about 10.0 mm, and most preferably from about 0.3 mm to about 3.0 mm. The term "particle diameter" refers to the longest dimension of the particle, which for spherical particles is the actual diameter while for non-spherical particles is the length or largest linear dimension.

Impregnation of the granules with hydrogen cyanamide can be achieved by methods known in the art. According to one convenient method, the hydrogen cyanamide can be added to the bare granules as a solution in a volatile solvent under conditions permitting the solution to be absorbed by the pores of the granules, and the solvent then allowed to evaporate by exposure to dry air, heat, or both. Any solvent can be used in which hydrogen cyanamide is soluble and that is chemically inert to the hydrogen cyanamide as well as to any other active ingredients or additives to be absorbed simultaneously and to the granule itself. Organic solvents can be used, examples of which are benzene, ethanol and other low molecular weight alcohols, and ethyl acetate, but water can be used as well and is preferred for its convenience and low cost. Aqueous solutions of hydrogen cyanamide are commercially available. One example is DORMEX® (a registered trademark of SKW Trostberg AG, and available from Degussa AG, Trostberg, Germany), which is a 50% by weight aqueous solution of hydrogen cyanamide.

In the practice of this invention, granules impregnated as described above are applied to soil or to crop growth media in general to control organisms that are considered deleterious to crop growth. These organisms include, but are not limited to, insects, nematodes, fungi, and undesired vegetation. The term "undesired vegetation" denotes non-crop plant species that otherwise tend to grow in the areas where crops are planted, and includes both volunteer crops and weeds. The undesired vegetation whose control is of greatest interest in the practice of this invention are weeds, and primarily those weeds associated with common crops such as corn, green peppers, tomatoes, soybeans, and vegetables in general, as well as cotton, sorghum, wheat, alfalfa, various ornamentals, and various turfgrasses. Nematodes that are deleterious to crop growth are plant-parasitic nematodes that include reniform nematodes (*Rotylenchulus reniformus*), spiral nematodes (*Helicotylenchus dihystera*), root-knot nematodes (*Meloidogyne arenaria*, *M. naasi* and *M. incognita*), stubby root nematodes (*Paratrichodorus minor*), stunt nematodes (*Tylenchorhynchus claytoni*), and others. These are distinct from nematodes that are beneficial to crop growth, examples of which are microbivorous (free-living) nematodes and other nematodes, such as those of the *Dorylaimida* order, that feed on algae, fungi, and other nematodes. The term "controlling" is used herein to denote either reducing the growth rate of the organisms, preventing the organisms from maturing, preventing the organisms from reproducing, or killing or reducing the viable population of the organisms. The term "pesticidally effective amount" is used herein to denote any amount of a treatment chemical that will produce any of these results.

The types of soils in which the formulations of this invention can be effective are sandy soils, loamy soils, clays, silt, and combinations such as sandy loam, silty loam, sandy clay, and the like. When the formulations are used for controlling undesirable vegetation, effective results can be achieved with both pre-emergence application (application to the soil before the undesirable vegetation emerges from the soil surface) and post-emergence application (application to the undesirable vegetation that has already emerged). Useful methods of application include broadcast or localized dusting or dry spraying, or soil tilling, or both. The application rates of the active ingredients to the soil can vary over a wide range. The optimal application rates will depend on the crop to be protected, the nature of the infestation, whether it be insect, nematode, or weed infestation, the stage of growth of the crop and of the infestation, and the manner in which application is made. For best results in controlling nematodes, the rate of application of hydrogen cyanamide will range from about 20 to about 500, and preferably from about 30 to about 300, kilograms per hectare. For best results in controlling weeds and other undesirable vegetation, the rate of application of hydrogen cyanamide will range from about 20 to about 500, and preferably from about 30 to about 300, kilograms per hectare. The same rates of application apply for controlling other types of infestation.

The following examples are offered for purposes of illustration and are not intended to limit the scope of the invention.

EXAMPLES OF HERBICIDAL ACTIVITY

These examples compare the herbicidal activity of hydrogen cyanamide as an impregnated granule to that of hydrogen cyanamide in liquid form, in pre-emergence application to soil seeded with a series of common weeds germinating in covered pots. The weeds used in these tests were grown from a standard weed seed pack of common annual and perennial weeds representing an extreme weed situation. The weeds included yellow nutsedge (*Cyperus esculentus*), crabgrass (*Digitaria sanguinalis*), sicklepod (*Senna obtusifolia*), morningglory (*Ipomoea* spp.), and other annual weeds. Observations of the effects on the weed population as a whole were made, and individual observations were made for yellow nutsedge, morningglory, sicklepod, and crabgrass.

The liquid hydrogen cyanamide solution was prepared immediately before use by dissolving solid hydrogen cyanamide in demineralized water to achieve a 2.5% by weight stock solution. The impregnated granules were prepared by mixing DORMEX (50% hydrogen cyanamide in aqueous solution with phosphate buffer) with PROFILE granules (15 mesh), and drying the resulting wet granules at 23° C. for 24 hours, to achieve final impregnated granules containing 25% hydrogen cyanamide by weight. Planting pots of polyvinyl chloride measuring 10 cm in diameter, each containing 1 kg of soil, were used. The soil was silt loam from a cotton field, pH 6.2, CEC<10 meq/100 g soil, organic matter <1.0%. For the liquid application tests, the aqueous stock solution was diluted further as needed such that 100 mL of the dilution contained the desired amount of hydrogen cyanamide for each test. The dilutions were then applied to the soil surface in each pot at 100 mL per pot. The dilutions were selected to achieve target application rates expressed in milligrams of hydrogen cyanamide per kilogram of soil, with 1 milligram of hydrogen cyanamide per kilogram of soil being approximately equal to 2 kilograms of hydrogen cyanamide per hectare of crop area or 2 pounds of hydrogen cyanamide per acre of crop area. For the granule application tests, the granules were placed on the soil surface and were then perfused with 100 mL of water to leach hydrogen cyanamide into the soil.

For both aqueous solution and granule formulations, the pots were covered immediately after treatment by a thick (1.5 mil), clear, low-density polyethylene bag held tightly against the outer wall of the pot by an elastic band. Six days after application of the treatments, the bags were removed, and the pots were left exposed as the weeds were allowed to grow. Weed counts were then taken at intervals of 6, 8, 12, and 18 days after application of the treatments. The treatments were arranged in randomized complete block design with seven replications per treatment, and statistical evaluation of the data was performed with analyses of variances (ANOVA) and standard regression procedures. Fischer's Least Significant Difference at p 0.05 was calculated when appropriate. The results, expressed in weeds per pot, are listed in Tables I, II, III, IV, and V for all weeds, yellow nutsedge, morningglory, sicklepod, and crabgrass, respectively, and the results for the same weeds at 18 days only are plotted in FIGS. 1, 2, 3, 4, and 5.

TABLE I

Herbicidal Activity of Hydrogen Cyanamide
Against All Weed Species in Pre-Emergence Application
in Covered Pots
Comparison Between Solid and Liquid Formulations

| $H_2NCN$ Application Rate (mg/kg soil) | Granule Days After Treatment | | | | Aqueous Solution Days After Treatment | | | |
|---|---|---|---|---|---|---|---|---|
| | 6 | 8 | 12 | 18 | 6 | 8 | 12 | 18 |
| 0 | 17 | 20.5 | 26.5 | 28.3 | 17 | 20.5 | 26.4 | 28.3 |
| 50 | 7 | 10.3 | 20 | 21 | 6 | 14.4 | 24 | 23.3 |
| 100 | 1.1 | 2.8 | 11 | 13.2 | 0.6 | 1.8 | 12.6 | 15.2 |
| 150 | 0.2 | 0.8 | 5 | 7.4 | 0.2 | 1.6 | 6.6 | 8.1 |
| 200 | 0 | 1.7 | 6.5 | 10.1 | 0 | 1.6 | 5 | 7.2 |
| 250 | 0 | 1.0 | 3 | 5.4 | 0 | 0.1 | 2.3 | 3.7 |
| 3001 | 0 | 0 | 1.5 | 3 | 0 | 0.6 | 3.4 | 4 |

TABLE II

Herbicidal Activity of Hydrogen Cyanamide
Against Yellow Nutsedge in Pre-Emergence Application
in Covered Pots
Comparison Between Solid and Liquid Formulations

| $H_2NCN$ Application Rate (mg/kg soil) | Granule Days After Treatment | | | | Aqueous Solution Days After Treatment | | | |
|---|---|---|---|---|---|---|---|---|
| | 6 | 8 | 12 | 18 | 6 | 8 | 12 | 18 |
| 0 | 0 | 1.5 | 2.5 | 3.0 | 0 | 1.5 | 2.5 | 3.0 |
| 50 | 0 | 1.4 | 2.0 | 3.1 | 0 | 1.6 | 2.7 | 2.7 |
| 100 | 0 | 0.6 | 1.9 | 2.3 | 0 | 0.9 | 2.0 | 2.6 |
| 150 | 0 | 0.3 | 2.0 | 2.4 | 0 | 0.7 | 1.7 | 1.9 |
| 200 | 0 | 1.0 | 2.9 | 3.2 | 0 | 1.3 | 1.6 | 2.3 |
| 250 | 0 | 0.9 | 2.0 | 3.2 | 0 | 0.1 | 0.7 | 0 |
| 300 | 0 | 0 | 0.7 | 0.3 | 0 | 0.6 | 1.3 | 0.4 |

TABLE III

Herbicidal Activity of Hydrogen Cyanamide
Against Morningglory in Pre-Emergence Application in Covered Pots
Comparison Between Solid and Liquid Formulations

| $H_2NCN$ Application Rate (mg/kg soil) | Weeds Per Pot: Morningglory | | | | | | | |
|---|---|---|---|---|---|---|---|---|
| | Granule | | | | Aqueous Solution | | | |
| | Days After Treatment | | | | | | | |
| | 6 | 8 | 12 | 18 | 6 | 8 | 12 | 18 |
| 0 | 7.4 | 7.0 | 5.9 | 5.9 | 7.4 | 7.0 | 5.9 | 5.9 |
| 50 | 1.0 | 1.1 | 1.6 | 1.3 | 0.4 | 0.7 | 0.9 | 0.6 |
| 100 | 0.1 | 0.1 | 0.3 | 0.3 | 0.1 | 0.1 | 0.1 | 0.1 |
| 150 | 0 | 0 | 0.1 | 0.1 | 0 | 0 | 0 | 0 |
| 200 | 0 | 0 | 0 | 0 | 0 | 0 | 0 | 0 |
| 250 | 0 | 0 | 0 | 0 | 0 | 0 | 0 | 0 |
| 300 | 0 | 0 | 0 | 0 | 0 | 0 | 0 | 0 |

TABLE IV

Herbicidal Activity of Hydrogen Cyanamide
Against Sicklepod in Pre-Emergence Application in Covered Pots
Comparison Between Solid and Liquid Formulations

| $H_2NCN$ Application Rate (mg/kg soil) | Weeds Per Pot: Sicklepod | | | | | | | |
|---|---|---|---|---|---|---|---|---|
| | Granule | | | | Aqueous Solution | | | |
| | Days After Treatment | | | | | | | |
| | 6 | 8 | 12 | 18 | 6 | 8 | 12 | 18 |
| 0 | 6.8 | 4.5 | 5.0 | 5.8 | 6.8 | 4.5 | 5.0 | 5.8 |
| 50 | 2.9 | 2.7 | 4.0 | 4.3 | 3.3 | 4.1 | 4.4 | 5.3 |
| 100 | 1.0 | 1.4 | 3.0 | 3.3 | 0.3 | 0.4 | 1.7 | 2.3 |
| 150 | 0.1 | 0.1 | 0.7 | 1.2 | 0 | 0.1 | 1.0 | 1.9 |
| 200 | 0 | 0.1 | 1.1 | 2.3 | 0 | 0.3 | 0.9 | 1.6 |
| 250 | 0 | 0 | 0.1 | 0.7 | 0 | 0 | 0.4 | 1.0 |
| 300 | 0 | 0 | 0 | 0.6 | 0 | 0 | 0.3 | 0.9 |

TABLE V

Herbicidal Activity of Hydrogen Cyanamide
Against Crabgrass in Pre-Emergence Application in Covered Pots
Comparison Between Solid and Liquid Formulations

| $H_2NCN$ Application Rate (mg/kg soil) | Weeds Per Pot: Crabgrass | | | | | | | |
|---|---|---|---|---|---|---|---|---|
| | Granule | | | | Aqueous Solution | | | |
| | Days After Treatment | | | | | | | |
| | 6 | 8 | 12 | 18 | 6 | 8 | 12 | 18 |
| 0 | 4.0 | 7.8 | 12.5 | 13.5 | 6.8 | 7.8 | 12.5 | 13.5 |
| 50 | 3.3 | 5.0 | 12.3 | 12.3 | 2.4 | 8.0 | 16.0 | 13.0 |
| 100 | 0 | 0.8 | 5.5 | 7.3 | 0.3 | 1.3 | 9.0 | 10.5 |
| 150 | 0.1 | 0.3 | 2.0 | 3.7 | 0.1 | 0.7 | 4.0 | 4.7 |
| 200 | 0 | 0.5 | 3.4 | 4.0 | 0 | 0.5 | 3.6 | 3.5 |
| 250 | 0 | 0 | 0.8 | 1.3 | 0 | 0 | 1.0 | 1.7 |
| 300 | 0 | 0 | 0.8 | 1.0 | 0 | 0 | 1.5 | 1.7 |

The results indicate that weed control with the granular formulation was equivalent to that obtained with the liquid preparation. Dosage response with either formulation accords well with standard dosage response models.

EXAMPLES OF NEMATICIDAL ACTIVITY

These examples demonstrate the nematicidal activity of hydrogen cyanamide as an impregnated granule applied to a silt loam in a covered pot, followed fifteen days later by the planting of soybean seeds in the soil. The soil used in this study was naturally infested with three species of nematodes, one of which was deleterious, and the other two beneficial, and observations were made of both the survival of the nematodes and the growth of the soybean plants.

The hydrogen cyanamide granules were prepared by impregnating PROFILE granules (15 mesh) with DORMEX (50% hydrogen cyanamide in aqueous solution with phosphate buffer), and drying the moist granules on trays at 20° C. for 24 hours to achieve granules containing hydrogen cyanamide at a concentration of 25% by weight. Planting pots measuring 10 cm in diameter were used. Each pot contained 1 kg of silt loam from a cotton field, pH 6.2, CEC<10 meq/100 g soil, organic matter<1.0%, the soil being severely infested with the deleterious reniform nematode (*Rotylenchulus reniformis*). Treatments of the soil with the granules were performed by spreading the granules on the surface of the soil in each pot at selected application rates, and then drenching the soil in 100 mL of water. The application rates ranged from zero to 500 mg active ingredient (hydrogen cyanamide) per kilogram of soil, with 1 mg/kg of soil being approximately equal to 2 kilograms of the active ingredient per hectare of soil or 2 pounds of the active ingredient per acre of soil.

Figure 1:
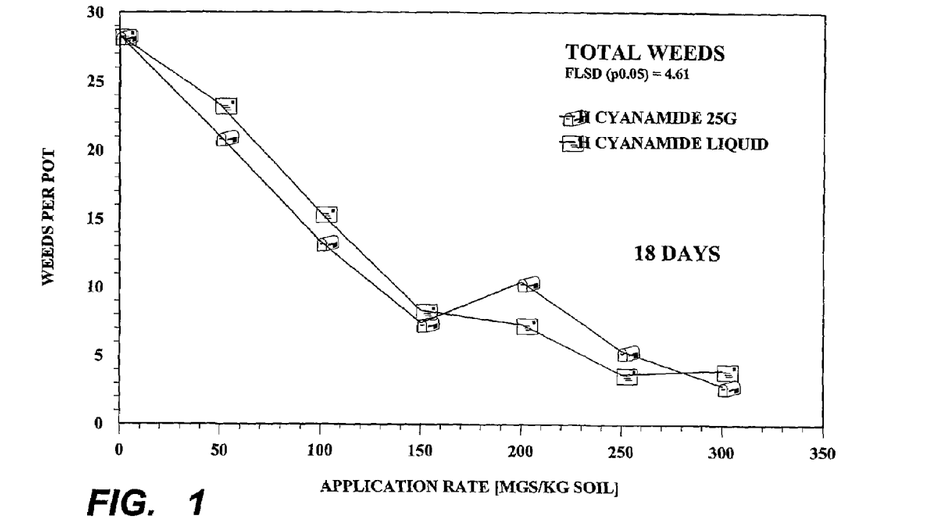
FIG. 1 is a plot of test results on a collective group of common crop weeds, comparing granular formulations in accordance with this invention with liquid formulations and showing herbicidal activity in pre-emergence application.
Figure 2:
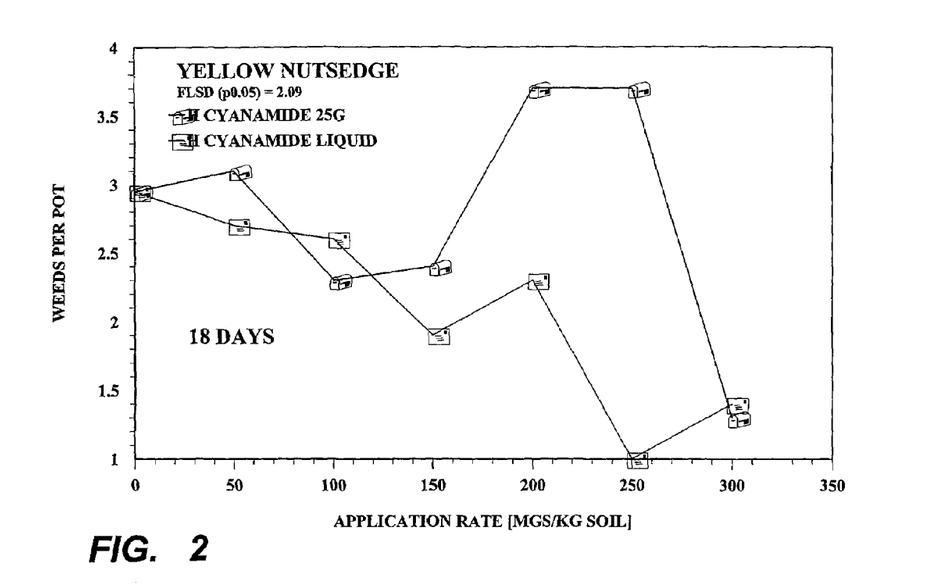
FIG. 2 is a plot of test results on yellow nutsedge, comparing granular formulations in accordance with this invention with liquid formulations and showing herbicidal activity in pre-emergence application.
Figure 3:
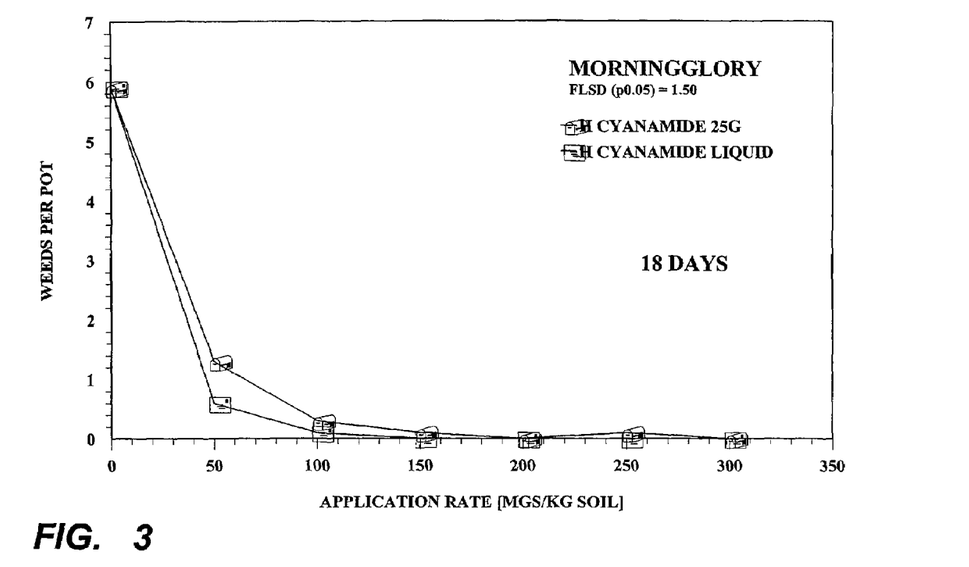
FIG. 3 is a plot of test results on morningglory, comparing granular formulations in accordance with this invention with liquid formulations and showing herbicidal activity in pre-emergence application.
Figure 4:
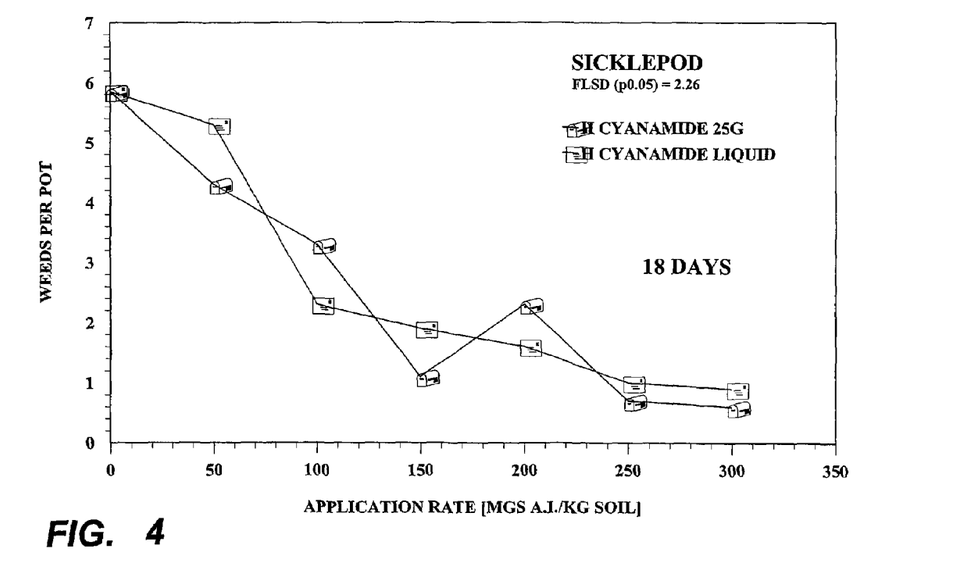
FIG. 4 is a plot of test results on sicklepod, comparing granular formulations in accordance with this invention with liquid formulations and showing herbicidal activity in pre-emergence application.
Figure 5:
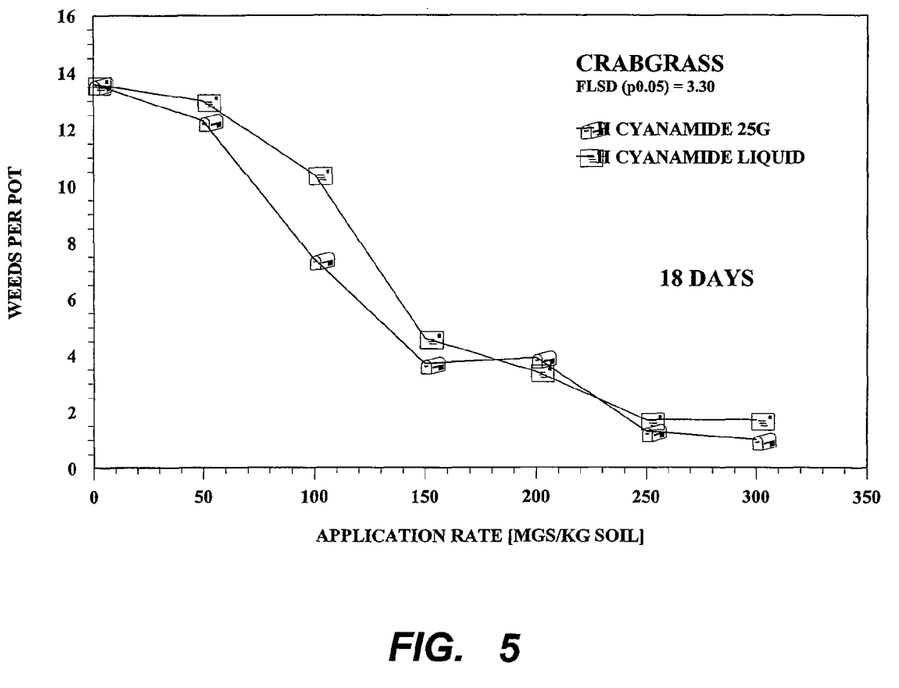
FIG. 5 is a plot of test results on crabgrass, comparing granular formulations in accordance with this invention with liquid formulations and showing herbicidal activity in pre-emergence application.
Figure 6:
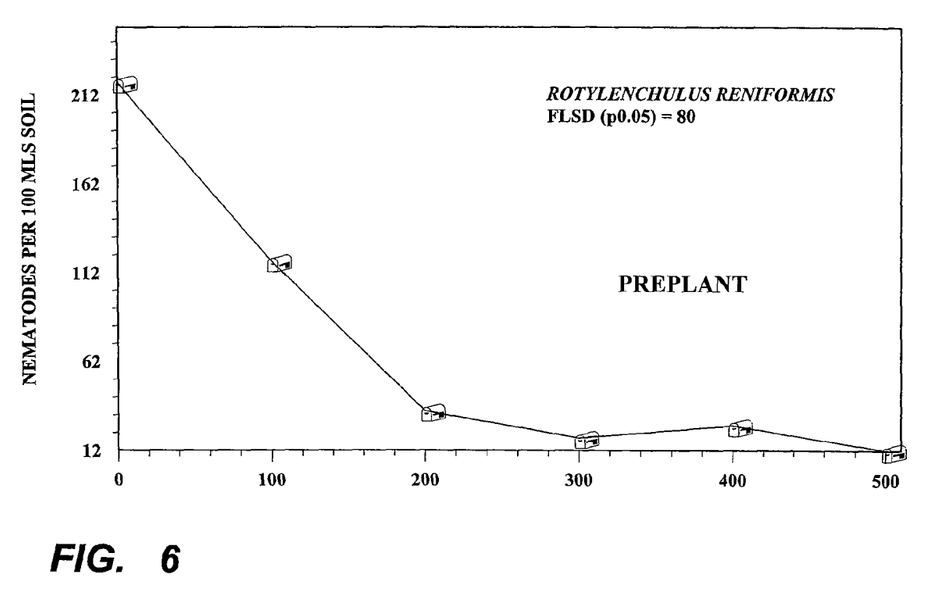
FIG. 6 is a plot of test results on nematodes using granular formulations in accordance with this invention on soil prior to planting of soybeans.

Immediately after the granules and water were applied, each pot was covered by a thick (1.5 mil), clear, low-density polyethylene bag. After fifteen days, the bags were removed and soil samples were taken from each pot for nematological analysis by the salad bowl technique of Rodriguez-Kabana, R., and M. H. Pope, *Nematropica*, 11: 175-186 (1981). The results of these analyses for the reniform nematodes, together with those for *Dorylaimida* nematodes (beneficial nematodes that are predatory, but not plant parasitic) and for microbivorous (beneficial) nematodes, all as pre-plant test results, are in Table VI. The results for the reniform nematodes are also shown as a plot of the number of nematodes vs. the hydrogen cyanamide application rate in FIG. 6.

TABLE VI

Nematicidal Activity of Hydrogen Cyanamide Granules
Pre-Plant Test Results: 15 Days After
Treatment and Prior to Crop Planting

| Cyanamide Application Rate (mg/kg soil) | Number of Surviving Nematodes per 100 mL of Soil | | |
|---|---|---|---|
| | Deleterious Nematodes | Beneficial Nematodes | |
| | Reniform | Dorylaimida | Microbivorous |
| 0 | 219 | 20 | 61 |
| 100 | 118 | 14 | 79 |
| 200 | 34 | 4 | 49 |
| 300 | 19 | 1 | 38 |
| 400 | 26 | 0 | 13 |
| 500 | 12 | 0 | 16 |

Figure 7:
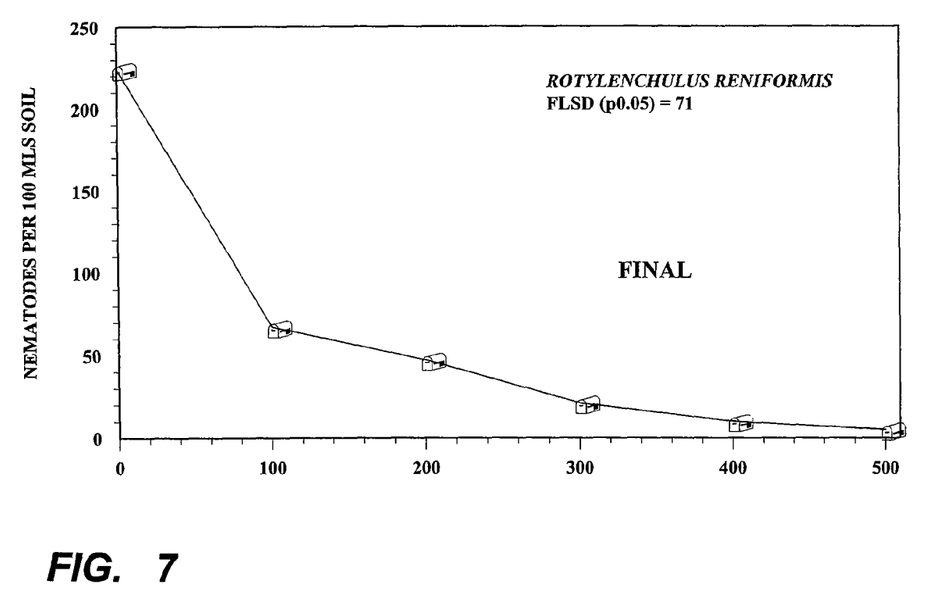
FIG. 7 is a plot of test results on nematodes, using granular formulations in accordance with this invention on soil prior to planting of soybeans, the results taken after the emergence of soybeans.

After the polyethylene bags were removed, each pot was planted with Hutcheson soybean seeds at 5 seeds per pot, and the seeds were allowed to germinate and the plants to grow for 39 days. The resulting plants were then removed from the pots and the root systems were washed. The number of surviving nematodes in each pot were determined, as were the number of nematodes in the root systems, the weights of both the fresh shoots and the roots, and the shoot height. Treatments were arranged in randomized complete block design with seven replications per treatment, and statistical evaluation of the data was performed with analyses of variance (ANOVA) and standard regression procedures. Fischer's Least Significant Difference at p 0.05 was calculated when appropriate. The results of these tests are listed as final test results in Tables VII, VIII, and IX. The results in terms of the surviving reniform nematodes per pot are also shown as a plot of the number of nematodes vs. the hydrogen cyanamide application rate in FIG. 7.

TABLE VII

Nematicidal Activity of Hydrogen Cyanamide Granules
56 Days After Treatment and 39 Days After Crop Planting

| Cyanamide Application Rate | Number of Surviving Nematodes per 100 mL of Soil | | |
|---|---|---|---|
| | Deleterious Nematodes | Beneficial Nematodes | |
| (mg/kg soil) | Reniform | Dorylaimida | Microbivorous |
| 0 | 224 | 30 | 329 |
| 100 | 67 | 2 | 168 |
| 200 | 47 | 4 | 237 |
| 300 | 21 | 2 | 383 |
| 400 | 10 | 0 | 372 |
| 500 | 5 | 0 | 218 |

TABLE VIII

Nematodes in the Root System
56 Days After Treatment and 39 Days After Crop Planting

| Cyanamide Application Rate | Number of Surviving Nematodes in Root System Per Pot | |
|---|---|---|
| (mg/kg soil) | Reniform | Microbivorous |
| 0 | 48 | 286 |
| 100 | 32 | 299 |
| 200 | 10 | 222 |
| 300 | 19 | 132 |
| 400 | 5 | 256 |
| 500 | 1 | 228 |

TABLE IX

Crop (Soybean) Conditions:
56 Days After Treatment and 39 Days After Crop Planting

| Cyanamide Application Rate (mg/kg soil) | Shoot Height (cm) | Weight of Fresh Shoots (g) | Weight of Fresh Roots (g) |
|---|---|---|---|
| 0 | 38.6 | 30.8 | 13.8 |
| 100 | 43.1 | 23.6 | 11 |
| 200 | 49.3 | 36 | 16.4 |
| 300 | 51.3 | 32.8 | 13.45 |
| 400 | 49 | 34.3 | 16.5 |
| 500 | 51 | 31.7 | 17.2 |

The pre-plant and final test results collectively indicate that hydrogen cyanamide can be applied in granular form without loss of nematicidal activity against the reniform nematodes, and that while the populations of the *Dorylaimida* nematodes were affected the populations of the microbivorous nematocides were not significantly affected. The granules exhibited dose relationships against the nematodes and plant growth responses similar to those obtained with liquid formulations. The granules also produced increases in shoot height and in the weights of the roots and the shoots. The granule formulation was as active as liquid formulations against nematodes.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein and an explicit teaching of this specification is intended to be resolved in favor of the teaching in this specification. This includes any discrepancy between an art-understood definition of a word or phrase and a definition explicitly provided in this specification of the same word or phrase.

We claim:

1. A composition for controlling organisms in soil that are deleterious to crop growth, said composition comprising hydrogen cyanamide retained in pores of porous solid granules that are chemically inert to hydrogen cyanamide.

2. The composition of claim 1 wherein said hydrogen cyanamide is the sole biologically active ingredient.

3. The composition of claim 1 wherein said composition comprises hydrogen cyanamide in the absence of other herbicides and insecticides.

4. The composition of claim 1 wherein said hydrogen cyanamide constitutes from about 10% to about 80% by weight of said composition.

5. The composition of claim 1 wherein said hydrogen cyanamide constitutes from about 20% to about 60% by weight of said composition.

6. The composition of claim 1 wherein said porous solid granules are calcined clay granules with a pore space of from about 30% to about 90%, or which at least about 20% is capillary porosity.

7. The composition of claim 1 wherein said porous solid granules are calcined clay granules with a pore space of from about 50% to about 90%, of which at least about 40% is capillary porosity.

8. The composition of claim 1 wherein said porous solid granules are calcined clay granules with a pore space of from about 60% to about 85%, of which from about 40% to about 80% is capillary porosity.

9. The composition of claim 1 wherein at least about 75% of said porous solid granules have particle diameters of from about 0.1 mm to about 10.0 mm.

10. The composition of claim 1 wherein said porous solid granules have a cation exchange capacity of from about 10 meq/100 g to about 75 meq/100 g.

11. A method for treating soil to control organisms in said soil that are deleterious to crop growth, said method comprising applying to said soil a pesticidally effective amount of a composition comprising hydrogen cyanamide retained in pores of porous solid granules that are chemically inert to hydrogen cyanamide.

12. The method of claim 11 wherein said hydrogen cyanamide is the sole biologically active ingredient.

13. The method of claim 11 wherein said composition comprises hydrogen cyanamide in the absence of other herbicides and insecticides.

14. The method of claim 11 wherein said hydrogen cyanamide constitutes from about 10% to about 80% by weight of said composition.

15. The method of claim 11 wherein said hydrogen cyanamide constitutes from about 20% to about 60% by weight of said composition.

16. The method of claim 11 wherein said porous solid granules are calcined clay granules with a pore space of from about 30% to about 90%, or which at least about 20% is capillary porosity.

17. The method of claim 11 wherein said porous solid granules are calcined clay granules with a pore space of from about 50% to about 90%, of which at least about 40% is capillary porosity.

18. The method of claim 11 wherein at least about 75% of said porous solid granules have particle diameters of from about 0.3 mm to about 3.0 mm.

19. The method of claim 11 wherein at least about 75% of said porous solid granules have particle diameters of from about 0.5 mm to about 1.0 mm.

20. The method of claim 11 wherein said porous solid granules have a cation exchange capacity of from about 10 meq/100 g to about 75 meq/100 g.

21. The method of claim 11 wherein said organisms are undesirable vegetation.

22. The method of claim 11 wherein said organisms are nematodes.

23. The method of claim 21 wherein said composition is applied at a rate that delivers from about 30 to about 300 kilograms of hydrogen cyanamide per hectare.

24. The method of claim 21 comprising applying said composition to said soil prior to emergence of said undesirable vegetation.

25. The method of claim 21 comprising applying said composition to said soil after emergence of said undesirable vegetation.

* * * * *